(12) United States Patent
Jeffrey et al.

(10) Patent No.: US 7,862,541 B2
(45) Date of Patent: Jan. 4, 2011

(54) CATHETER HAVING A SOFT DISTAL TIP

(75) Inventors: Andrew Jeffrey, Tuebingen (DE); Louise Balfe, Stuttgart (DE); Lorcan Coffey, Tuebingen (DE); Arik Zucker, Zurich (CH); Kay Unzicker, Jestetten (DE); Zdravkica Dzakula, Buelach (CH); Ib Joergensen, Haigerloch (DE); Randolf von Oepen, Los Altos Hills, CA (US)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 635 days.

(21) Appl. No.: 11/766,662

(22) Filed: Jun. 21, 2007

(65) Prior Publication Data

US 2008/0004568 A1 Jan. 3, 2008

Related U.S. Application Data

(63) Continuation-in-part of application No. 10/296,252, filed as application No. PCT/EP01/05893 on May 22, 2001, now abandoned, application No. 11/766,662, which is a continuation-in-part of application No. 11/335,931, filed on Jan. 20, 2006.

(60) Provisional application No. 60/646,118, filed on Jan. 21, 2005.

(30) Foreign Application Priority Data

May 22, 2000 (DE) ................................ 200092049

(51) Int. Cl.
*A61M 29/00* (2006.01)
(52) U.S. Cl. .................... 604/96.01; 606/194
(58) Field of Classification Search ................. 604/103, 604/194
See application file for complete search history.

(56) References Cited

U.S. PATENT DOCUMENTS 4,725,264 A 2/1988 Glassman (Continued)

FOREIGN PATENT DOCUMENTS

EP 0277368 8/1988

(Continued)

OTHER PUBLICATIONS

U.S. Appl. No. 60/646,118, filed Jan. 21, 2005, Jeffrey et al.

(Continued)

*Primary Examiner*—Nicholas D Lucchesi
*Assistant Examiner*—Ian K Holloway
(74) *Attorney, Agent, or Firm*—Workman Nydegger

(57) ABSTRACT

The present invention relates to a catheter having a soft distal tip that can be manufactured at lower cost than catheters in the prior art. In one embodiment, the catheter is produced by coupling a soft sleeve to the distal end of a catheter tube. The sleeve may affixed to the catheter tube under temperature and pressure conditions that cause the proximal end of the sleeve to taper against the outer surface of the catheter tube, avoiding or minimizing discontinuities in the insertion profile of the catheter, and that also cause the inner wall of the sleeve to taper against the distal end of the catheter tube, avoiding or minimizing discontinuities in the lumen of the catheter.

27 Claims, 4 Drawing Sheets

U.S. PATENT DOCUMENTS

| | | | |
|---|---|---|---|
| 4,782,834 A | | 11/1988 | Maguire et al. |
| 4,921,483 A | * | 5/1990 | Wijay et al. ............... 604/103.1 |
| 5,100,381 A | | 3/1992 | Burns |
| 5,250,060 A | | 10/1993 | Carbo et al. |
| 5,304,134 A | | 4/1994 | Kraus et al. |
| 5,334,148 A | | 8/1994 | Martin |
| 5,425,712 A | | 6/1995 | Goodin |
| 5,728,065 A | | 3/1998 | Follmer et al. |
| 5,964,778 A | * | 10/1999 | Fugoso et al. ................ 606/194 |
| 6,010,521 A | | 1/2000 | Lee et al. |
| 6,146,395 A | | 11/2000 | Kanz et al. |
| 6,268,315 B1 | | 7/2001 | Baca et al. |
| 6,368,301 B1 | | 4/2002 | Hamilton et al. |
| 6,368,315 B1 | | 4/2002 | Gillis et al. |
| 6,575,934 B2 | * | 6/2003 | Duchamp ............... 604/102.02 |
| 6,702,802 B1 | * | 3/2004 | Hancock et al. ............. 604/524 |
| 6,893,416 B2 | | 5/2005 | Guinan et al. |
| 6,960,188 B2 | | 11/2005 | Jorgensen |
| 7,115,137 B2 | * | 10/2006 | Duchamp ................... 606/194 |
| 2002/0072705 A1 | | 6/2002 | Vrba et al. |
| 2003/0032921 A1 | * | 2/2003 | Duchamp ................... 604/103 |
| 2003/0114794 A1 | * | 6/2003 | Duchamp .............. 604/103.06 |
| 2003/0139760 A1 | | 7/2003 | Stamberg |
| 2003/0139761 A1 | | 7/2003 | Jorgensen et al. |
| 2006/0071371 A1 | * | 4/2006 | Quint et al. .................. 264/512 |
| 2007/0282367 A1 | | 12/2007 | Jeffrey et al. |

FOREIGN PATENT DOCUMENTS

| | | |
|---|---|---|
| WO | 99/44666 | 9/1999 |
| WO | WO 01/89620 | 11/2001 |

OTHER PUBLICATIONS

U.S. Appl. No. 10/296,252, Mail Date Jul. 15, 2004, Office Action.
U.S. Appl. No. 10/296,252, Mail Date Dec. 30, 2004, Office Action.
U.S. Appl. No. 10/296,252, Mail Date Jun. 21, 2005, Office Action.
U.S. Appl. No. 10/296,252, Mail Date Nov. 2, 2005, Office Action.
U.S. Appl. No. 10/296,252, Mail Date Apr. 28, 2006, Office Action.
U.S. Appl. No. 10/296,252, Mail Date Jul. 11, 2006, Office Action.
U.S. Appl. No. 10/296,252, Mail Date Dec. 21, 2006, Office Action.
U.S. Appl. No. 11/335,931, Mail Date Jan. 21, 2009, Office Action.
U.S. Appl. No. 11/335,931, Mail Date Apr. 28, 2009, Office Action.
U.S. Appl. No. 11/335,931, Mail Date Dec. 30, 2009, Office Action.

* cited by examiner

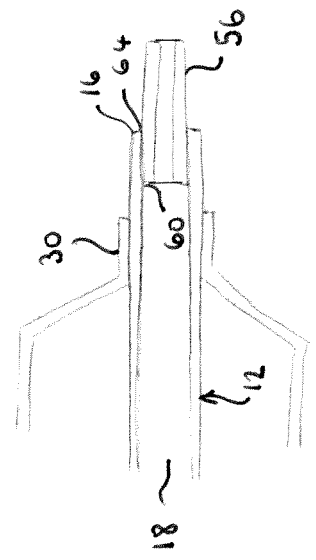
FIG. 5
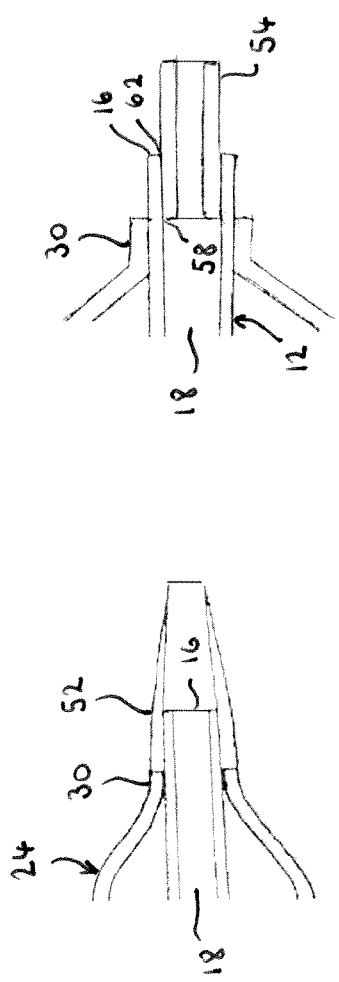
FIG. 6
FIG. 6A
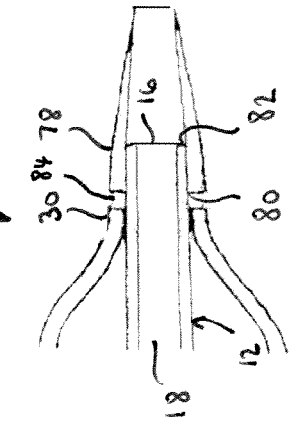
FIG. 7
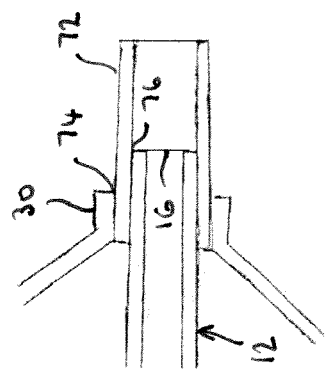
FIG. 8
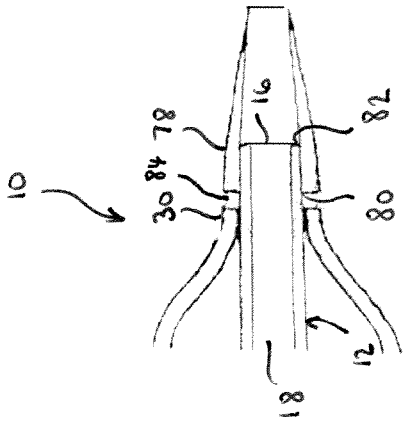
FIG. 9

CATHETER HAVING A SOFT DISTAL TIP

CROSS-REFERENCE TO RELATED APPLICATIONS

The present application is a continuation-in-part of U.S. application Ser. No. 10/296,252, filed on Nov. 21, 2002, which claims priority to PCT application no. PCT/EP01/05893, filed on May 22, 2001, which claims priority to German application no. 200092049, filed on May 22, 2000, the entireties of which are incorporated herein by reference. The present application is also the continuation-in-part of U.S. application Ser. No. 11/335,931, filed on Jan. 20, 2006, which claims priority to provisional application Ser. No. 60/646,118, filed on Jan. 21, 2005, the entireties of which are incorporated herein by reference.

FIELD OF THE INVENTION

The present invention relates to a catheter having a soft distal tip and to methods of manufacture thereof. More particularly, the present invention relates to a catheter having a soft distal tip and to methods of manufacture, in which the soft distal tip is formed by affixing a soft sleeve to the distal end of a catheter tube.

BACKGROUND OF THE INVENTION

Since its introduction in 1977, angioplasty has become a widely used procedure for the treatment of vascular disease. A common forms of angioplasty is coronary angioplasty, also known as "percutaneous transluminal coronary angioplasty," in which a balloon catheter is inserted into a blocked artery to remove a stenosis.

During coronary angioplasty, the catheter is inserted into a blood vessel either at the elbow or at the groin. The catheter is then pushed inside the blood vessel until the point of blockage in the artery has been reached. A balloon disposed at the tip of the catheter then expands the narrowed artery and allows blood to flow normally through the artery after the procedure. Optionally, a stent is coupled to the balloon, so that the stent expands when the balloon is inflated, supporting the wall of the vessel after the balloon has been removed and maintaining patency.

A catheter suitable for angioplasty procedures must be sufficiently flexible to wind through tight curvatures, for example, in the coronary arteries, but at the same time must be "pushable," or be able to transmit a longitudinal pressure along its length, so that a clinician can force the catheter through the vascular system and to the target location by applying a controlled amount of pressure at the proximal end of the catheter. The development of new materials has brought to market a new generation of catheters that provide the desired degree of "pushability" and trackability while enabling a considerable reduction in cross-sectional diameter.

A risk associated with catheters having an elevated degree of "pushability" is vessel injury or rupture. Additionally, a stiff catheter tip may cause endothelial abrasion by rubbing against the wall of the vessel.

To minimize these risks, catheters have been developed that include a soft distal tip, so to provide for a less traumatic contact with a vessel wall. Examples of prior art catheters having soft tips are disclosed U.S. Pat. No. 4,921,483 to Wijay et al.; U.S. Pat. No. 5,100,381 to Burns; U.S. Pat. No. 5,334,148 to Martin; U.S. Pat. No. 5,728,065 to Follmer et al.; U.S. Pat. No. 6,325,790 to Trotta; U.S. Pat. No. 6,368,301 and U.S. Pat. No. 6,837,869 to Hamilton et al.; U.S. Pat. No. 6,702,802 to Hancock et al.; U.S. Pat. No. 6,979,342 to Lee et al.; U.S. Pat. No. 6,999,809 to Currier et al.; and U.S. Pat. No. 7,115,137 to Duchamp. Such prior art catheters are manufactured by producing the tip as a separate component shaped for coupling with the catheter tube without discontinuities along the profile of the catheter, that is, without altering either the outer diameter or the lumen of the catheter, so that the insertion profile of the catheter is not modified and so that a guide wire reciprocating within the lumen does not encounter obstacles along its travel. The soft tips of those catheters are generally manufactured with a number of recesses that mate with the catheter body and with the distal end of the catheter balloon. Unfortunately, this process is costly because specially shaped tips must be produced and carefully coupled with the other components of the catheter, so that the various surfaces and recesses properly mate one with the other.

BRIEF SUMMARY OF THE INVENTION

In one embodiment, a catheter having a soft distal tip is manufactured by disposing a soft sleeve over the distal end of a catheter tube and by extending a portion of the sleeve beyond the distal end of the catheter tube. The sleeve is essentially free of recesses before being coupled with the distal end of the catheter tube. The sleeve is finally affixed to the surface of the catheter tube, under temperature and pressure conditions that cause the outer surface of the sleeve at its proximal end to taper against the outer surface of the catheter tube, avoiding or minimizing discontinuities in the insertion profile of the catheter tube. At the same time, process conditions also cause the inner wall of the sleeve to soften and taper against the distal end of the catheter tube, minimizing or eliminating discontinuities at the point of transition between the lumen of the catheter and the lumen of the sleeve.

In another embodiment, the manufacturing process of a catheter having a soft distal tip according to the present invention also includes disposing an inflatable balloon over the distal end of the catheter tube. In variants of this embodiment, the proximal end of the sleeve may abut or overlay the distal neck of the balloon, or the distal neck of the balloon may overlay the sleeve partially or entirely. In another variant of this embodiment, the distal neck of the balloon is longitudinally spaced from the sleeve.

Prior to coupling with the catheter tube, the sleeve may have an essentially cylindrical or essentially frusto-conical shape, or may have a frusto-conical shape stretched around the catheter tube to assume a cylindrical shape at the proximal end and a frusto-conical shape at the distal end. The thickness of the sleeve wall may be constant or variable, for example, may progressively taper from its proximal end to its distal end.

In still another embodiment of the present invention, a catheter having a soft distal tip is manufactured by disposing a soft sleeve inside the catheter lumen and by extending a portion of the sleeve beyond the distal end of the catheter tube. The lateral wall of the sleeve is essentially free of recesses prior to coupling to the lateral wall of the lumen and is then affixed in the lumen, for example by welding. If welding is performed under appropriate temperature and pressure conditions, the proximal end of the sleeve tapers against the wall of the lumen, reducing or eliminating any steps between the lumen wall and the sleeve wall.

In yet another embodiment of the present invention, a soft sleeve is affixed inside a catheter lumen and is aligned or offset at its proximal end from the distal end of a balloon. The soft sleeve may also be essentially cylindrical or frusto-conical in shape, or may be stretched to be cylindrical in shape at the proximal end and frusto-conical at the distal end. The thickness of the wall of the sleeve may be constant or variable, tapering from a larger thickness at the proximal end to a smaller thickness at the distal end of the sleeve.

BRIEF DESCRIPTION OF THE SEVERAL VIEWS OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

FIG. 5 is a cross-sectional view of the distal end of a catheter according to yet another embodiment of the invention.

FIGS. 6 and 6A are cross-sectional views of the distal end of a catheter according to more embodiments of the invention.

FIG. 7 is a cross-sectional view of the distal end of a catheter according to still another embodiment of the invention.

FIG. 8 is a cross-sectional view of the distal end of a catheter according to yet another embodiment of the invention.

FIG. 9 is a cross-sectional view of the distal end of a catheter according to one more embodiment of the invention.

DETAILED DESCRIPTION OF EMBODIMENTS OF THE INVENTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Figure 1:
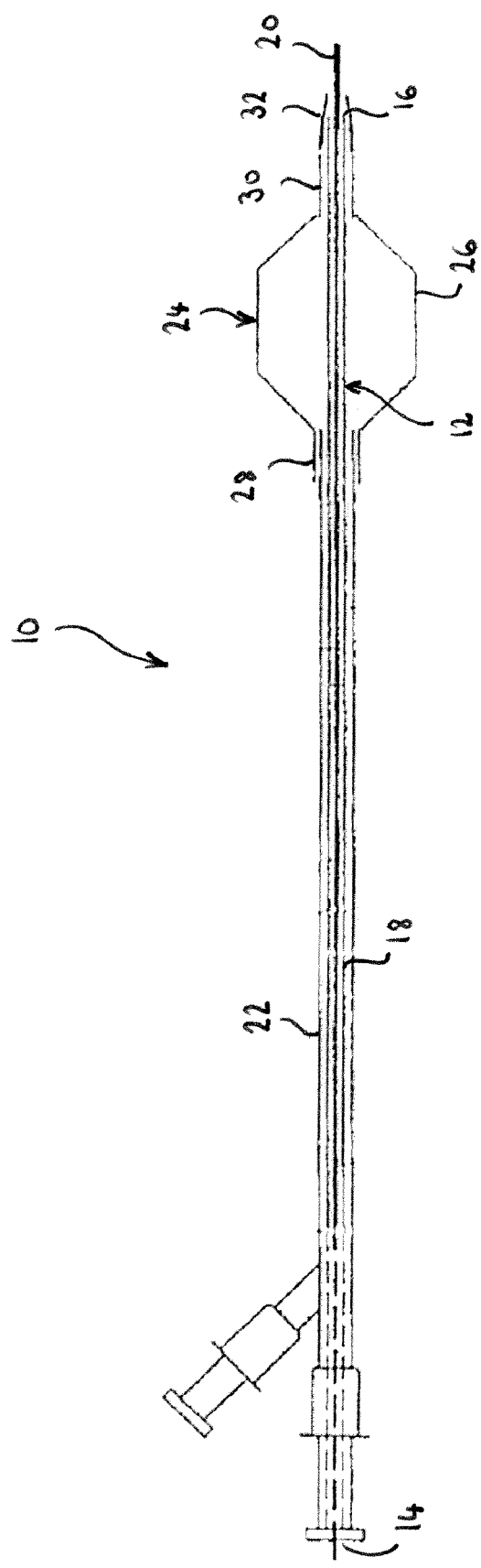
FIG. 1 is a schematic side view of a catheter having a soft distal tip.

FIG. 1 schematically depicts a catheter having a soft distal tip, which is adapted for use in angioplasty procedures. It should be understood that the catheter of FIG. 1 represents one of several possible embodiments of the invention, and that the present invention is equally applicable to catheters adapted for non-angioplasty procedures and also to catheters that do not include inflating balloons, for example, catheters structured for use with self-expanding stents.

Catheter 10 includes a catheter tube 12 having a proximal end 14, a distal end 16, and a lumen 18 extending between proximal end 14 and distal end 16. "Distal end" is defined herein as the distal tip of the catheter tube and the portion of the catheter tube immediately adjacent thereto. Catheter tube 12 is configured to enable the passage and the longitudinal translation of guide wire 20 within lumen 18 during a surgical procedure.

Outer tube 22 is disposed either concentrically or parallel to catheter tube 12 and is configured to carry an inflation fluid (for example, a saline solution) to and from inflatable balloon 24. In turn, balloon 24 is formed by a body 26, configured to expand upon ingress of the inflation fluid, a proximal neck 28, affixed (for example, welded or bonded) to outer tube 22, and a distal neck 30, affixed to catheter tube 12.

Catheter tube 12 can be produced from a variety of materials, including metal, plastic and composite materials. In one embodiment, catheter tube 12 is manufactured as a metal tube, for example, as a stainless steel hypotube, and may be coated with a polymeric material such as PTFE. The metal tube may also be covered with a single or multilayered plastic material through one or more processes, including coextrusion, dipping, heat-shrinking, and electrostatic and thermal coating.

In another embodiment, catheter tube 12 is manufactured as a plastic tube. Materials suitable for use in the catheter tube include but are not limited to Polyurethanes (PU), such as Tecoflex, Pellethene, Bionate, corethane, Elasteon, and blends thereof; Polyethylenes (PE), such as PET, PBT, PVDF, Teflon, ETFE, and blends thereof, Polyolefins, such as HDPE, PE, LDPE, LLDPE, Polypropylene, and blends thereof, Polyimides; Polyamides; all classes of Nylons, such as Nylon 11, Nylon 12, Nylon 6,6, Nylon 6, Nylon 7,11, Nylon 11,12, and blends thereof); block copolymers; PEBA-types polymers, such as ELY, PEBAX, Ubesta, and blends thereof, and biodegradable polymers. Suitable materials also include blends of the above mentioned materials as well as any composite materials, like dual-layers, tri-layers and multi-layers thereof. For example, catheter tube 12 may be produced from a tube comprising an outer layer made of Nylon and an inner layer made of a lubricious material such as polyethylene or PTFE. A metallic or nonmetallic braiding may also be included within or between layers of the catheter tube 12.

Conversely, Outer tube 22 may be produced from a material or a combination of materials equal or different from those of catheter tube 12.

Disposed at distal end 16 of catheter tube 12 is soft tip 32, which provides for an atraumatic contact between catheter tube 12 and a wall against which catheter tube 12 may be pushed during a surgical procedure. Soft tip 32 is composed of a soft sleeve that is affixed on and that extends beyond distal end 16, or, alternatively, that is affixed on and extends beyond the lumen of catheter tube 12. Typically, soft tip 32 is affixed through a welding process, but other affixing techniques are also included within the scope of the present invention, for example, adhesive bonding. Suitable materials for the sleeve can be chosen from any material suitable for producing catheter tube 12, as described above.

FIGS. 2A to 9 depict a number of representative embodiments of the invention, illustrating different, non-limiting arrangements of soft tip 32 in relation to catheter tube 12 and of balloon 24.

Figures 2B, 2C, 2D:
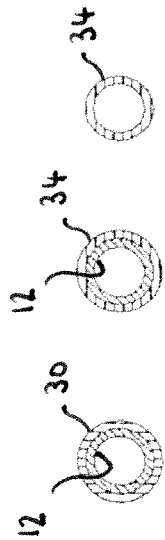
FIGS. 2B-2D are different cross-sectional views of the distal end of FIG. 2A.
Figure 2A:
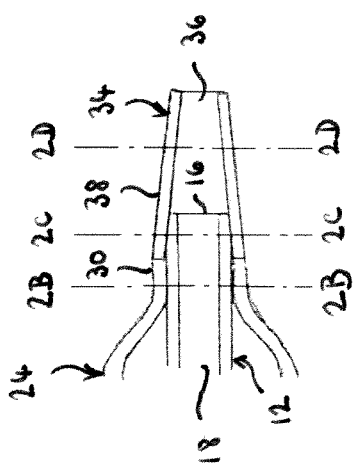
FIG. 2A is a cross-sectional view of the distal end of a catheter according to an embodiment of the invention.

Referring first to FIG. 2A, balloon 24 is disposed over catheter tube 12, with distal neck 30 affixed to the outer wall of catheter tube 12 and ending proximally of distal end 16. Sleeve 34 is affixed to distal end 16 and abuts proximally against distal neck 30, extending distally beyond distal end 16.

Sleeve 34 may be manufactured from a material softer than catheter tube 12, and may be formed from the same material as balloon 24 or from a different material, for example, from any of the materials or combinations of materials described with reference to catheter tube 12. In one embodiment, sleeve 24 is manufactured from a material having the same basic composition but a lower Shore durometer hardness than the balloon material or the catheter tube material. In another embodiment, sleeve 34 may be manufactured from a blend of PEBAX 55D and PEBAX 63D polymers. One skilled in the art will recognize that sleeve 34 may be manufactured from a variety of other materials according to the previous description of materials, for example, a polyurethane, a polyethylene, a polyolefin, a polyimide, a polyamide like Nylon, a block copolymer, or blends, or compositions or dual layers or multi-layers thereof.

FIGS. 2B-2D illustrate the arrangement of FIG. 2A in greater detail by depicting cross-sections of the assembly of FIG. 2A at three different section planes. More particularly, the cross-section of FIG. 2B illustrates the arrangement of FIG. 2A proximally of the soft sleeve, and includes catheter tube 12 and distal neck 30. The cross-section of FIG. 2C illustrates the arrangement of FIG. 2A in the proximal portion of sleeve 34 and includes both catheter tube 12 and sleeve 34. Because distal neck 30 does not overlap sleeve 34, but rather one abuts against the other, no cross-section of distal neck 30 can be seen in FIG. 2C. The cross-section of FIG. 2D illustrates the arrangement of FIG. 2A in the distal portion of sleeve 34 and only shows a cross-section of sleeve 34, because at cross-section 2D sleeve 34 extends beyond distal end 16 of catheter tube 12.

Prior to coupling with catheter tube 12, sleeve 34 may be essentially cylindrical in shape or have a frusto-conical profile. In one embodiment, sleeve 34 has an essentially frusto-conical profile but is stretchable enough so that, when sleeve 34 is disposed over distal end 16, the proximal portion of sleeve 34, in contact with distal end 16, deforms to assume an essentially cylindrical configuration, while the distal part of sleeve 34, extending beyond distal end 16, retains an essentially frusto-conical profile. Regardless of its external profile, sleeve 34 includes a lumen 36 defined by a lateral wall 38, and prior to the coupling of sleeve 34 with distal end 16, sleeve 16 is essentially free of recesses, so that sleeve 34 can be fitted and affixed over distal end 16, for example, by a welding or a bonding process. In this respect, sleeve 34 is different from sleeves or soft tips employed in the prior art, the design of which is based on recesses on the lateral wall of the soft tip, in order to achieve a configuration of the catheter tube-sleeve assembly that guarantees that the lumen and the outer profile of the catheter retain a constant diameter.

Figure 2E:
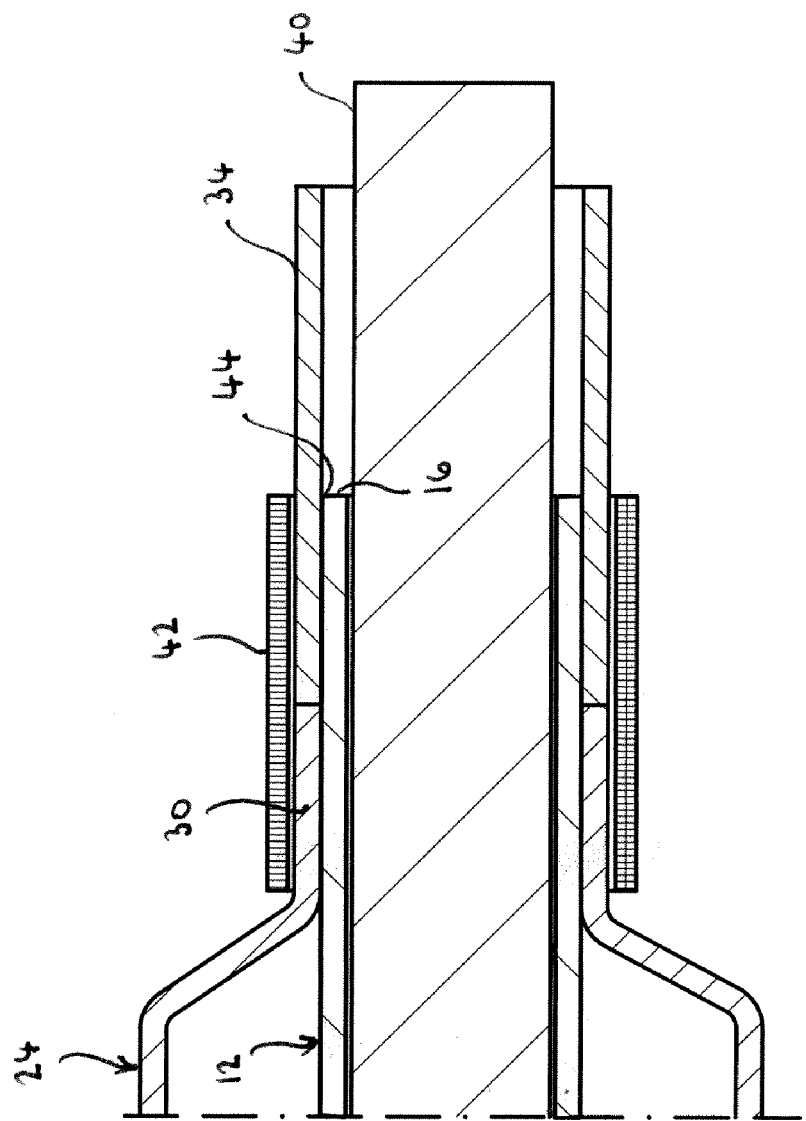
FIG. 2E is a cross-sectional cutaway view of the distal end of a catheter according to an embodiment of the invention.

Referring now to FIG. 2E, an embodiment of a process for affixing sleeve 34 over distal end 16 is shown. Catheter tube 12, balloon 24 and sleeve 34 are assembled over a mandrel 40, and a shrink tube 42 is disposed at least over the assembly portion that includes distal end 16, distal neck 30 and a proximal portion of the sleeve 34. In another embodiment, shrink tube 12 covers distal end 16, distal neck 30 and sleeve 34. Shrink tube 42 may be manufactured from a material that will prevent a permanent adhesion of shrink tube 42 against neck 30 and sleeve 34, so that shrink tube 42 can be easily removed (for example, by peeling off) at the end of the welding process. Equally, mandrel 40 may be manufactured from or coated with a material that will not adhere to the inner wall of sleeve 34 during the welding process. During the successive welding process, shrink tube 42 applies pressure against distal neck 30 and at least a portion of sleeve 34. Such a pressure may be applied either by having shrink tube 42 contract over distal neck 30 and sleeve 34, for example, due to the application of vacuum or heat, or shrink tube 42 may maintain a constant diameter while mandrel 40 expands due to the application of heat, thereby applying pressure against distal neck 30 and sleeve 34.

In one embodiment, sleeve 34 has an inner diameter substantially equal or nearly equal to the outer diameter of catheter tube 12, to facilitate positioning of sleeve 34 over the distal portion of catheter tube 12. In this embodiment, shrink tube 42 will cover distal end 16, distal neck 30 and sleeve 34, thereby forcing the sleeve down to the mandrel during welding process. This will result in a constant inner diameter of the guide wire lumen 18 as further described below. In another embodiment, the inner diameter of the sleeve 34 is equal to the inner diameter of catheter tube 12 and the proximal portion of the sleeve 34 is stretched over the distal end of the catheter tube when catheter tube 12, balloon 24 and sleeve 34 are assembled on the mandrel.

The above described combination of heat and pressure causes the materials of distal neck 30 and of sleeve 34 to soften and weld to catheter tube 12. At the same time, the combination of such softening and of the pressure applied on distal neck 30 and sleeve 34 causes the joint between distal neck 30 and sleeve 34 to become essentially smooth, minimizing or preventing the formation of protrusions or steps when distal neck 30 and sleeve 34 have walls with different or uneven thickness. Likewise, step 44 between distal end 16 and sleeve 34 is reduced and, under proper operating conditions, eliminated due to the softening of the sleeve material, facilitating the translation of guide wire 20 (not shown in FIG. 2A) along lumen 18.

The welding process is performed by applying heat or radiation to the assembly, for example, by laser welding, hot jaw welding, transition bonder welding, hot air welding arc welding, RF welding or white light welding as described in U.S. Patent Publication No. 2006/0071371, which is incorporated by reference herein in its entirety. Heat may be applied to this assembly from the outside by an external energy source and/or from the inside by heating mandrel 40.

Figure 3:
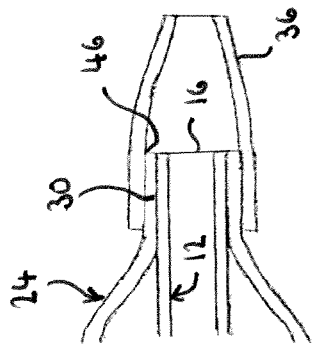
FIG. 3 is a cross-sectional view of the distal end of a catheter according to another embodiment of the invention.

FIG. 3 illustrates a second embodiment of the invention, in which sleeve 36 overlays both catheter tube 12 and distal neck 30. In this embodiment, distal neck 30 extends to the end of distal end 16, therefore, sleeve 36 is not welded to catheter tube 12, but rather is welded to distal neck 30, which in turn is welded to catheter tube 30. In this embodiment, sleeve 36 may be shaped in two main portions, a proximal portion having an essentially cylindrical shape that is welded to distal neck 30, and a distal portion having an essentially frusto-conical shape that extends beyond distal end 16. Alternatively, sleeve 36 may have an essentially frusto-conical configuration that is partially stretched to an essentially cylindrical shape in the area of contact with distal neck 30.

In order to achieve proper welding between sleeve 36 and distal neck 30, a mandrel and a shrink tube may employed as previously described. Also as previously described, one skilled in the art will recognize that the mandrel may be heated to achieve the desired welding, or heat may be provided from an external source, for example, by applying heat or radiation energy, also as previously described. The application of energy is adjusted in such a way that the proximal end of sleeve 36 may soften to provide a smooth transition between balloon 24 (or distal neck 33) and sleeve 36, and step 46 between catheter tube 12 and distal neck 30 on one side and the inner wall of sleeve 36 on the other side may be eliminated by the softening of sleeve 36 and distal neck 30 during the welding process.

Figure 4:
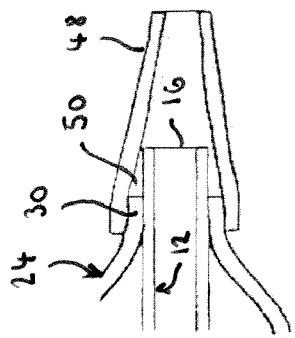
FIG. 4 is a cross-sectional view of the distal end of a catheter according to still another embodiment of the invention.

FIG. 4 illustrates a third embodiment, in which sleeve 38 is partially overlapping distal neck 30, which does not extend as far as distal end 16. In this embodiment, the softening of sleeve 48 causes not only a smoothing of the transition between the outer surface of balloon 24 and sleeve 48, but also causes a partial or total filling of interstice 50 between the inner wall of sleeve 48 and the outer wall of catheter tube 12. As in the preceding embodiment, sleeve 48 may have a cylindrical or frusto-conical shape or a combination thereof, and may be stretchable from its original configuration to a modified configuration.

FIG. 5 illustrates a further embodiment of the invention, in which sleeve 52 is disposed distally of distal neck 30, and abuts the distal end of distal neck 30, similarly to the embodiment of FIG. 2A. When the proximal portion of sleeve 52 is welded against the outer wall of distal end 16, the combined action of the mechanical pressure exercised on sleeve 52 (for example, by applying a shrink tube against distal end 16 and by inserting a mandrel within lumen 18) and of thermal or radiation energy applied to the assembly causes sleeve 52 to soften and to provide catheter 10 with a distal tip that is smooth both on its outer profile and at the transition between distal end 16 and sleeve 52. In this embodiment, sleeve 52 has a tapered wall, decreasing in thickness from its proximal end to its distal end. The above described application of heat and pressure, aimed at welding sleeve 52 to distal end 16 and at avoiding steps between distal neck 30 and sleeve 52, may reduce or eliminate such tapered shape in the portion disposed over distal end 16, and this effect is even more pronounced when sleeve 52 is stretchable. At the same time, the tapering of the distal portion of sleeve 52 causes the distal tip of sleeve 52 to be extremely soft, with softness decreasing as one moves proximally of the distal tip.

FIGS. 6 and 6A depict different embodiments of the present invention, in which sleeves 54 and 56 are partially disposed not over the outer wall of catheter tube 12, but instead within lumen 18 to extends outwards of catheter tube 12. The difference between the embodiments of FIGS. 6 and 6A is that, in the embodiment of FIG. 6, the proximal end of sleeve 54 is substantially laterally aligned with the distal end of distal neck 30, while in the embodiment of FIG. 6A the proximal end of sleeve 56 is laterally offset from the distal end of distal neck 30, providing for a portion of catheter tube 12 to span between the distal end of distal neck 30 and the proximal end of sleeve 56. By comparing the embodiments of FIGS. 6 and 6A, one skilled in the art will notice that the embodiment of FIG. 6 provides for a more constant wall thickness of the catheter tip because at each point of distal end 16 a double wall is present, either provided by distal neck 30 and catheter tube 12, or by catheter tube 12 and sleeve 54, while in the embodiment of FIG. 6A a distance exists between the neighboring ends of distal neck 30 and of sleeve 56, in which only the wall of catheter tube 12 is present. Steps 58 and 60, at the joint between sleeve 54 and respectively 56 and the inner wall of lumen 16, are minimized and possibly eliminated during the welding process of sleeves 54 and respectively 56 against the wall of lumen 18, for example, by disposing a mandrel within sleeves 54 or 56, and by causing the mandrel to expand radially by heating the mandrel or by imposing a shrink tube over the assembly, and by causing the shrink tube to shrink down by applying heat to the assembly. This reduction or elimination of steps 58 and 60 facilitates the translation of a guide wire (not shown) within lumen 16 by reducing or eliminating recesses, in which the guide wire may become entangled. Likewise, steps 62 and 64 also may be reduced or substantially eliminated during the welding process of sleeves 54 and respectively 56 by the same deformation process of sleeves 54 and respectively 56. In the embodiment depicted in FIG. 6A, the input of welding energy can be adjusted in a way to causes the steps to be totally eliminated, thus providing a thinner wall thickness that with the embodiment depicted in FIG. 6. In one embodiment, sleeves 54 and respectively 56 have the same inner diameter as catheter tube 12. During assembly, the distal portion of the catheter tube will then be stretched and disposed over a proximal portion of the sleeve 54 and 56, respectively.

Referring now to the embodiment depicted in FIG. 7, distal neck 30 extends beyond distal end 16 of catheter tube 12, and entirely surrounds sleeve 66, extending beyond the distal end of sleeve 66. Therefore, the distal tip of catheter 10 in this embodiment exhibits a decreasing flexibility moving proximally from the distal end of catheter 12 (which corresponds to the distal end of distal neck 30) to a catheter portion, in which distal neck 30 encircles sleeve 66, and more proximally to a catheter portion, in which distal neck 30 encircles sleeve 66 and also distal end 16. As for the previous embodiments, step 68 at the junction point of distal end 16 with sleeve 66 is partially or entirely removed during the welding process of sleeve 66 to catheter tube 12 and distal neck 30, providing a smoother contour along the translation path of a guide wire within lumen 18 and through the distal portion of distal neck 30. Step 70 may also be partially or completely removed during the welding process.

Referring now to FIG. 8, an additional embodiment of the present invention is depicted, in which sleeve 72 is disposed between distal neck 30 and catheter tube 12, and in which sleeve 72 has a proximal end substantially aligned with the proximal end of distal neck 30, and a distal end extending beyond distal end 16 of catheter tube 12. In variants of the present embodiment, the proximal end of sleeve 72 may be offset proximally or distally in relation to the proximal end of distal neck 30. As in the previously described embodiments, the welding process of sleeve 72 to distal neck 30 and catheter tube 12 may cause a partial or total elimination of steps 74 and 76, due to the softening of distal neck 30 and/or of sleeve 72. Also, as in the previous described embodiments, the inner diameter of sleeve 72 may be equal to the inner diameter of catheter tube 12 and the proximal portion of sleeve 72 will be stretched over the distal catheter tube portion, or inner diameter of sleeve 72 may be close to the outer diameter of the catheter tube 12, and sleeve 72 is shrunk down on a mandrel, to result in a constant inner diameter of the tube along the whole length by applying pressure with a shrink tube during the welding process.

Referring now to FIG. 9, still another embodiment of the present invention is depicted that includes a sleeve 78, disposed at proximal end 16 of catheter tube 12 and distally of distal neck 30. In this embodiment, distal neck 30 and sleeve 78 are spaced longitudinally one from the other resulting in a gap 90, to provide catheter 10 with a more flexible distal tip in comparison, for example, to the embodiment illustrated in FIG. 5. As for the embodiment of FIG. 5, and for all other embodiments described herein, sleeve 78 has a tubular shape that may have a cylindrical or frusto-conical outer profile, and that may have an outer wall of constant or of narrowing thickness from the proximal end to the distal end of sleeve 78. Sleeve 78 may also be welded to distal tip 16 using process conditions that reduce or eliminate the presence of steps 80 and/or 82, facilitating the translation of a guide wire within lumen 18 and the sliding of catheter 10 within a vessel. By adjusting the input of heat, gap 84 can be eliminated to result in a smooth transition or gap 84 can be preserved with a reduced or rounded step 80, thereby providing a kind of hinge joint to the catheter tip.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

What is claimed is:

1. A method of manufacturing a balloon catheter having a soft distal tip, the balloon catheter having an outer tube and an inner tube extending within at least a distal portion of the outer tube, and spaced apart from at least a portion of the outer tube to form an inflation lumen therebetween, and a balloon disposed adjacent the distal end of the balloon catheter, the method comprising:

placing a distal neck portion of the balloon over a distal portion of the inner tube so as to leave at least part of the distal portion of the inner tube extending beyond the distal neck portion of the balloon;

placing a sleeve over the extended part of the distal portion of the inner tube so that the sleeve contacts the distal neck portion of the balloon, the sleeve being formed of a material that is soft in relation to the inner tube so as to provide a soft, flexible navigation tip once the balloon catheter is formed, and a portion of the sleeve extending beyond the distal portion of the inner tube;

placing a shrink tube over the distal neck portion of the balloon and a portion of the sleeve, the shrink tube terminating at the distal end of the inner tube, and portions of the distal neck and sleeve that are covered by the shrink tube forming an essentially uniform outer circumference, and said portion of the sleeve extending beyond the distal portion of the inner tube also extending beyond the distal end of the shrink tube;

placing a mandrel through the center of the inner tube so that the mandrel extends beyond the distal end of the sleeve; and applying one or both of pressure and heat so that the distal neck portion and sleeve are bonded to the inner tube and the portion of the sleeve that extends beyond the distal portion of the inner tube essentially eliminates any step between the inner tube and the sleeve.

2. The method of claim 1, wherein the proximal end of the sleeve abuts the distal neck.

3. The method of claim 1, wherein the sleeve overlays the distal neck.

4. The method of claim 3, wherein the sleeve partially overlays and abuts an outer surface of the distal neck and partially overlays and abuts an outer surface of the catheter tube.

5. The method of claim 3, wherein the sleeve partially overlays the distal neck.

6. The method of claim 1, wherein the distal neck overlays the sleeve and extends beyond the distal end of the sleeve.

7. The method of claim 1, wherein the distal neck overlays the proximal end of the sleeve, and wherein the distal end of the sleeve extends beyond the distal neck.

8. The method of claim 1, wherein the proximal end of the sleeve is longitudinally spaced from the distal neck.

9. The method of claim 1, wherein a distal portion of the sleeve has an essentially frusto-conical shape prior to disposing the sleeve over the distal end of the catheter tube.

10. The method of claim 1, wherein the sleeve is stretchable and assumes an essentially cylindrical shape at the proximal end and an essentially frusto-conical shape at the distal end by having the proximal end of the sleeve stretch around the distal end of the catheter tube.

11. The method of claim 1, wherein the sleeve lateral wall tapers from a larger thickness at the proximal end of the sleeve to a smaller thickness at the distal end of the sleeve.

12. The method of claim 1, wherein the portion of the sleeve is affixed by welding.

13. A method of manufacturing a catheter having a soft distal tip, the balloon catheter having an outer tube and an inner tube extending within at least a distal portion of the outer tube, and spaced apart from at least a portion of the outer tube to form an inflation lumen therebetween, and a balloon disposed adjacent the distal end of the balloon catheter, the method comprising:

placing a distal neck portion of the balloon over a distal end portion of the inner tube;

placing a sleeve within the distal end portion of the inner tube, at least a portion of the sleeve extending beyond the inner tube and being formed of a material that is soft in relation to the inner tube so as to provide a soft, flexible navigation tip once the balloon catheter is formed;

placing a mandrel through the center of the inner tube so that the mandrel extends beyond the distal end of the sleeve; and applying one or both of pressure and heat so that the distal neck portion and sleeve are bonded to the inner tube and the portion of the sleeve that extends beyond the distal end portion of the inner tube essentially eliminates any step between the inner tube and the sleeve.

14. The method of claim 13, further comprising, placing a shrink tube over the distal neck portion of the balloon and at least that part of the inner tube into which the sleeve extends.

15. The method of claim 13, wherein the distal end of the sleeve is substantially laterally aligned with a distal end of the distal neck.

16. The method of claim 13, wherein the distal end of the sleeve is longitudinally offset from a distal end of the distal neck.

17. The method of claim 13, wherein the sleeve is essentially cylindrical or essentially frusto-conical in shape.

18. The method of claim 13, wherein the sleeve is essentially cylindrical in shape at the proximal end and essentially frusto-conical at the distal end, the sleeve lateral wall tapering from a larger thickness at the proximal end of the sleeve to a smaller thickness at the distal end of the sleeve.

19. The catheter of claim 13, wherein the portion of the sleeve is affixed by welding.

20. A balloon catheter comprising:

an outer tube; and an inner tube extending within at least a distal portion of the outer tube, and spaced apart from at least a portion of the outer tube to form an inflation lumen therebetween a balloon disposed adjacent a distal end of the balloon catheter; and a sleeve disposed inside the distal end of the balloon catheter, the sleeve being bonded to the inner tube, and, the sleeve being formed of a material that is soft in relation to the inner tube so as to provide a soft, flexible navigation tip once the balloon catheter is formed.

21. The balloon catheter of claim 20, wherein the proximal end of the sleeve is substantially laterally aligned with a distal end of the distal neck.

22. The balloon catheter of claim 20, wherein the distal end of the sleeve is longitudinally separated from a distal end of the distal neck.

23. The balloon catheter of claim 20, wherein the sleeve is essentially cylindrical or frusto-conical in shape.

24. The balloon catheter of claim 20, wherein the sleeve is essentially cylindrical in shape at the proximal end and essentially frusto-conical at the distal end, the sleeve lateral wall tapering from a larger thickness at the proximal end of the sleeve to a smaller thickness at the distal end of the sleeve.

25. The balloon catheter of claim 20, wherein the portion of the sleeve is affixed by welding.

26. The balloon catheter of claim 20 wherein a portion of the sleeve extends beyond the distal portion of the inner tube essentially without any step between the inner tube and the sleeve.

27. The method of claim 14, wherein said portion of the sleeve extends beyond the distal end portion of the inner tube that is covered by the shrink tube forming an essentially uniform circumference and also extending beyond the distal end of the shrink tube.

\* \* \* \* \*